United States Patent
Mohr et al.

(10) Patent No.: US 11,680,169 B2
(45) Date of Patent: Jun. 20, 2023

(54) INORGANIC EFFECT PIGMENTS

(71) Applicant: BASF COLORS & EFFECTS GMBH, Ludwigshafen am Rhein (DE)

(72) Inventors: Benjamin Mohr, Elmsford, NY (US); Christopher Sichmeller, Elmsford, NY (US)

(73) Assignee: Sun Chemical B.V., Weesp (NL)

( * ) Notice: Subject to any disclaimer, the term of this patent is extended or adjusted under 35 U.S.C. 154(b) by 0 days.

(21) Appl. No.: 16/500,668

(22) PCT Filed: Apr. 4, 2017

(86) PCT No.: PCT/US2017/025946
§ 371 (c)(1),
(2) Date: Oct. 3, 2019

(87) PCT Pub. No.: WO2018/186838
PCT Pub. Date: Oct. 11, 2018

(65) Prior Publication Data
US 2020/0115558 A1    Apr. 16, 2020

(51) Int. Cl.
*C09C 1/00* (2006.01)
*A61K 8/25* (2006.01)
(Continued)

(52) U.S. Cl.
CPC .......... *C09C 1/0066* (2013.01); *A61K 8/0266* (2013.01); *A61K 8/25* (2013.01);
(Continued)

(58) Field of Classification Search
CPC .......... A61K 8/0266; A61K 8/25; A61K 8/29; A61K 2800/438; A61K 2800/436;
(Continued)

(56) References Cited

U.S. PATENT DOCUMENTS 6,132,873 A    10/2000    Dietz et al.
6,596,070 B1    7/2003    Schmidt et al.
(Continued)

FOREIGN PATENT DOCUMENTS

CN    101671034 A    *    3/2010
CN    102876090 A        1/2013
(Continued)

OTHER PUBLICATIONS

International Search Report and Written Opinion in International Application No. PCT/US2017/025946, dated Nov. 27, 2017. (15 pages).

(Continued)

*Primary Examiner* — Shuangyi Abu Aliz
(74) *Attorney, Agent, or Firm* — Howard C. Lee (57) ABSTRACT

An inorganic, non-quarter wave, heterogeneous multilayer effect pigment includes a platy substrate comprising an absorbing optically active metal oxide layer thereon, having an optical thickness from about 20 nm to about 400 nm; a layer of low refractive index material on the absorbing optically active metal oxide layer and having an optical thickness from about 10 nm to about 500 nm; and an outermost optically active layer of a non-absorbing high refractive index material on the low refractive index material and having an optical thickness from about 50 nm to about 1000 nm. The multilayer effect pigment exhibits a blue reflectance ratio (BRR) of at least 3, according to the equation: BRR=(Blue Max)/(Green Min); where Blue Max is the maximum reflectance exhibited over wavelengths 380 nm to 450 nm; and Green Min is the minimum reflectance exhibited over wavelengths 450 nm to 600 nm.

11 Claims, 3 Drawing Sheets

(51) Int. Cl.
*A61K 8/29* (2006.01)
*A61K 8/02* (2006.01)
*A61Q 19/00* (2006.01)

(52) U.S. Cl.
CPC .............. *A61K 8/29* (2013.01); *A61Q 19/00* (2013.01); *C09C 2200/1033* (2013.01); *C09C 2200/302* (2013.01); *C09C 2200/303* (2013.01); *C09C 2200/306* (2013.01); *C09C 2220/106* (2013.01)

(58) Field of Classification Search
CPC ........ A61K 8/0254; A61K 8/26; A61Q 19/00; A61Q 1/02; C01P 2004/51; C01P 2006/65; C01P 2006/66; C01P 2004/54; C01P 2006/12; C01P 2006/62; C01P 2006/63; C01P 2006/64; C01P 2006/60; C09C 1/0039; C09C 1/0066; C09C 2200/102; C09C 2200/1033; C09C 2200/302; C09C 2200/303; C09C 2200/306; C09C 2220/106; C09C 3/06; C09C 1/0024; C09C 2200/307; C09D 11/037
See application file for complete search history.

(56) References Cited

U.S. PATENT DOCUMENTS

| | | |
|---|---|---|
| 6,599,355 B1 | 7/2003 | Schmidt et al. |
| 2004/0170838 A1 | 9/2004 | Ambrosius et al. |
| 2005/0166799 A1* | 8/2005 | Fuller .................. C09C 1/0024 106/415 |
| 2007/0015012 A1 | 1/2007 | Bujard et al. |
| 2007/0259182 A1 | 11/2007 | Bujard et al. |
| 2008/0011198 A1 | 1/2008 | Fu et al. |
| 2008/0279796 A1 | 11/2008 | Handrosch et al. |
| 2009/0090275 A1 | 4/2009 | Fu et al. |
| 2009/0185992 A1 | 7/2009 | Conan et al. |
| 2010/0015337 A1 | 1/2010 | Becker et al. |
| 2010/0021565 A1 | 1/2010 | Handrosch et al. |
| 2011/0226161 A1 | 9/2011 | Schumacher et al. |
| 2011/0237683 A1 | 9/2011 | Schmid et al. |
| 2011/0265689 A1* | 11/2011 | Schumacher .......... C09C 1/003 106/417 |
| 2012/0027993 A1 | 2/2012 | Schmid et al. |
| 2014/0251184 A1 | 9/2014 | Mcguire et al. |
| 2016/0280926 A1 | 9/2016 | Bujard et al. |

FOREIGN PATENT DOCUMENTS

| | | |
|---|---|---|
| JP | 2003-183538 A | 7/2003 |
| JP | 2010-207009 A | 9/2010 |
| JP | 2013-502466 A | 1/2013 |

OTHER PUBLICATIONS

Pfaff, Gerhard et al., "Special effect pigments in cosmetic applications," Household and Personal Care Today, Colour Cosmetics, 2012, vol. 7, No. 1, pp. 12-15.

* cited by examiner

Single Layer Fe$_2$O$_3$

FIG. 3

INORGANIC EFFECT PIGMENTS

CROSS-REFERENCE TO RELATED APPLICATIONS

This application is a U.S. National Phase Application under 35 U.S.C. § 371 of International Application No. PCT/US2017/025946, filed on Apr. 4, 2017, the contents of which are incorporated herein by reference in their entirety.

FIELD

The present technology is generally related to the field of effect pigments. More particularly, the technology relates to effect pigments in the red, fuchsia, and magenta color space.

SUMMARY

In one aspect, an inorganic, non-quarter wave, heterogeneous multilayer effect pigment includes: a platy substrate comprising an absorbing optically active metal oxide layer thereon, having an optical thickness from about 20 nm to about 400 nm; a layer of low refractive index material on the absorbing optically active metal oxide layer and having an optical thickness from about 10 nm to about 500 nm; and an outermost optically active layer of a non-absorbing high refractive index material on the low refractive index material and having an optical thickness from about 50 nm to about 1000 nm; wherein: the multilayer effect pigment exhibits a blue reflectance ratio (BRR) of at least 3, according to the equation: BRR=(Blue Max)/(Green Min); where Blue Max is the maximum reflectance exhibited over wavelengths 380 nm to 450 nm; and Green Min is the minimum reflectance exhibited over wavelengths 450 nm to 600 nm. In some embodiments, the platy substrate includes natural mica, synthetic mica, glass flakes, $SiO_2$, $Al_2O_3$, talc, bismuth oxychloride, natural pearl, perlite, boron nitride, zinc oxide, a natural silicate, a synthetic silicate, or a combination of any two or more thereof.

In another aspect, a method of producing an effect pigment includes coating a platy substrate with an optical coating comprising the following steps: depositing an absorbing optically active metal oxide layer on the platy substrate, the absorbing optically active metal oxide layer having an optical thickness of about 20 nm to 400 nm depositing a low refractive index material layer on the absorbing optically active metal oxide layer, the low refractive index material layer having an optical thickness of about 10 nm to about 500 nm; and depositing a non-absorbing high refractive index material layer on the low refractive index material layer, the non-absorbing high refractive index material layer having a thickness from about 50 nm to 100 nm; wherein: the effect pigment exhibits a blue reflectance ratio (BRR) of at least 3, according to the equation: BRR=(Blue Max)/(Green Min); wherein Blue Max is the maximum reflectance exhibited over wavelengths 380 nm to 450 nm; and Green Min is the minimum reflectance exhibited over wavelengths 450 nm to 600 nm. In some embodiments, the platy substrate includes natural mica, synthetic mica, aluminum, glass flakes, $SiO_2$, $Al_2O_3$, talc, bismuth oxychloride, natural pearl, perlite, boron nitride, zinc oxide, a natural silicate, a synthetic silicate, or a mixture of any two or more thereof.

In another aspect, a product includes any of the effect pigments described herein. For example, the product may be a cosmetic, an automotive coating, an industrial coating, ab ink, or a plastic.

DETAILED DESCRIPTION

Figure 1:
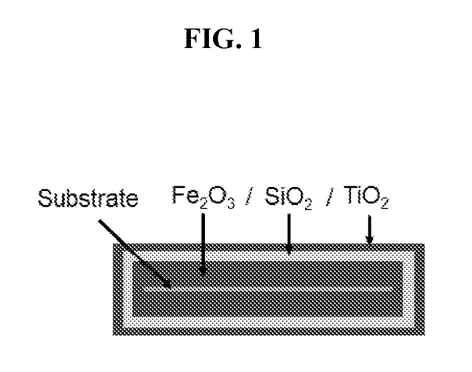
FIG. 1 is a schematic diagram of a pigment structure, according to one embodiment.
Figure 2:
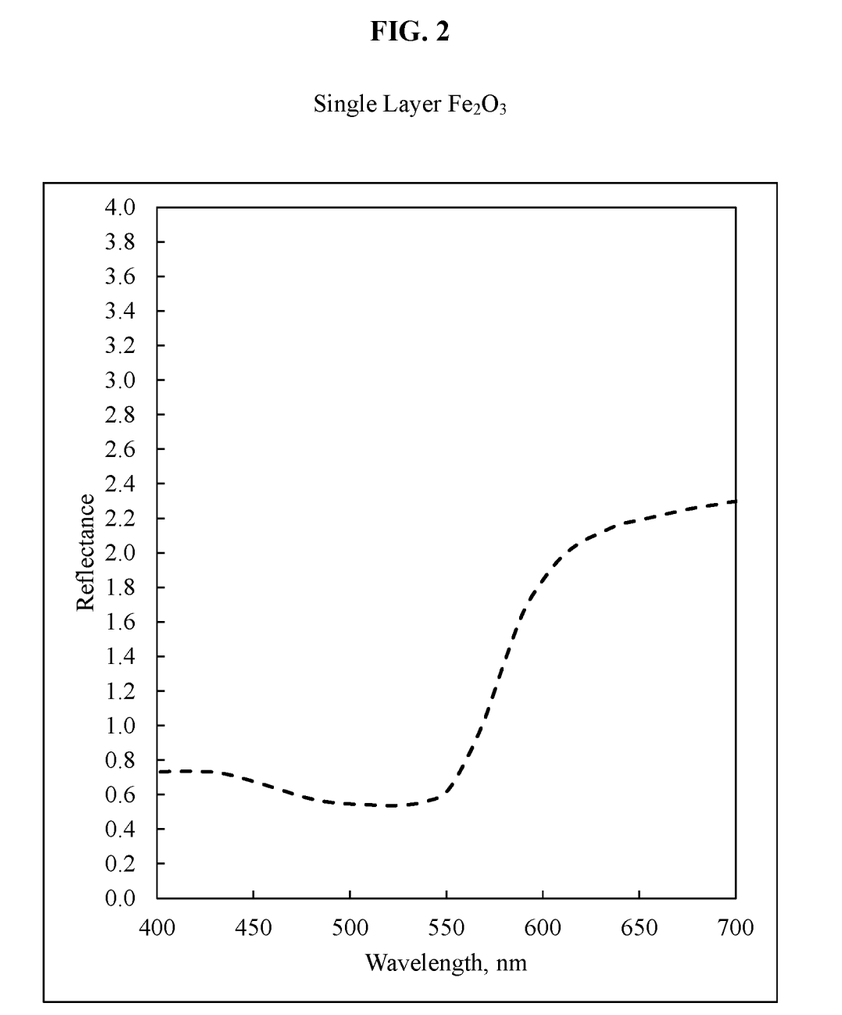
FIG. 2 is reflectance spectrum of a pigment containing a single layer of iron oxide on a mica substrate, according to a comparative example.
Figure 3:
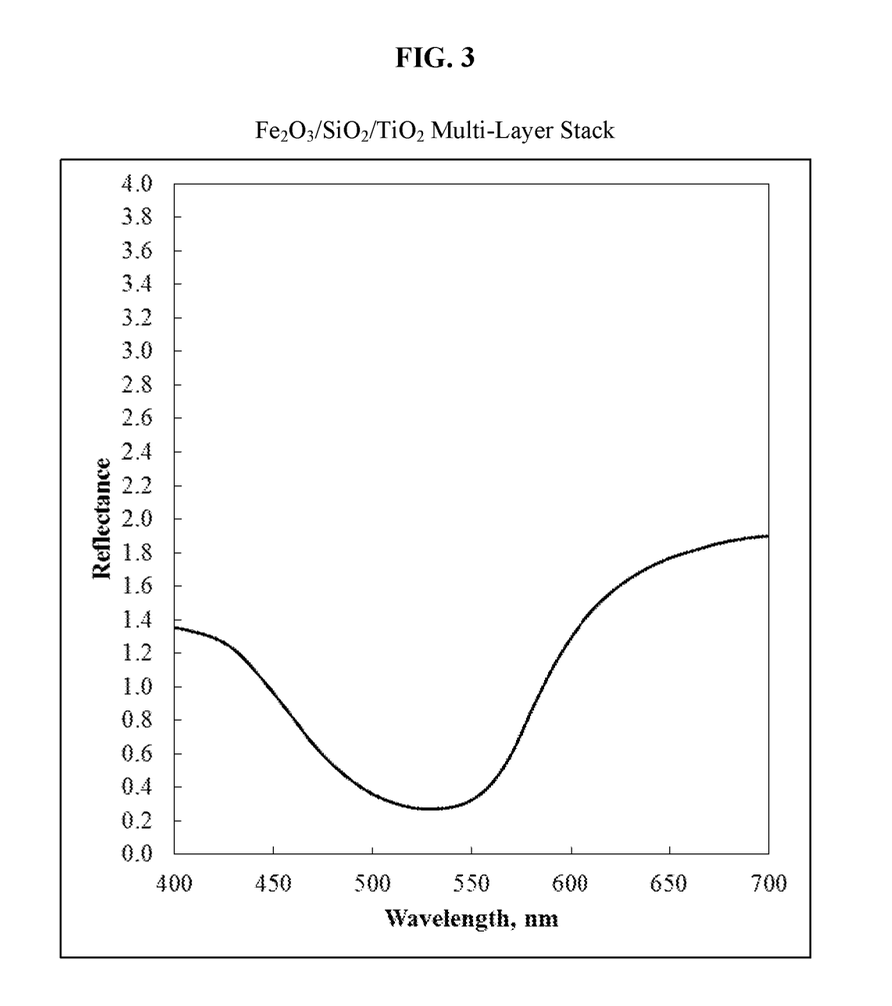
FIG. 3 is reflectance spectrum of a pigment containing a layer of iron oxide, a layer if silicon dioxide, and a layer of titania on a mica substrate, according to the examples.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "effect pigment" refers to a pigment that interacts with light by reflection and/or transmission and/or refraction.

As used herein, the descriptor "platy" is well understood in the art, and may be used interchangeably with flake, flake-like, plate-like, platelet, and flaky.

As used herein, the term "transparent" refers to a material or object that can transmit from at least about 75% to about 100% of visible light.

As used herein, the term "optical thickness" refers to the thicknesses of each of the individual layers applied to the substrate. Optical thickness is the product of the actual physical or geometric thickness (t) of the layer and the refractive index (n) of the material of the layer. While it may be possible to measure the physical thickness of the deposited layer on the substrate, the refractive index of the applied material will vary from published values depending on the density and uniformity of the deposited layer. The optical thickness can be indirectly determined by measuring the wavelengths at which interferences occur in the sample and then solving for "nt" in the well-known constructive interference and/or destructive interference equations. The equations, as written below, are for normal angle incidence of light only, in which the cosine θ term reduces to 1 and does not need to appear, in the interest of simplifying the present discussion.

Constructive interference equation:

$$nt = m\lambda/4, \text{ wherein}$$

m=odd integer
n=refractive index of the layer material
t=geometric (physical) thickness of the layer material, in nanometers
λ=the wavelength of maximum reflection, in nanometers
nt=optical thickness of the layer material, in nanometers Destructive interference equation:

$$nt = m\lambda/2, \text{ wherein}$$

m=any positive integer
λ=wavelength of the minimum reflection, in nanometers

By measuring the interference wavelength λ from samples having the desired color after each layer deposition, the optical thickness of each layer can be readily determined. It is important to note that in the present technology, the optical thicknesses of all the layers are not the same.

As used herein, the term "optically active" refers to the sufficient physical thickness to cause an optical discontinuity between adjoining layers of the same material such that an overall significantly observable change to the optical characteristics of the stack are achieved which would not be theoretically or practically possible without the presence of the optically active interlayer. Measureable changes in optical characteristics of effect pigments include percent reflectivity and chromaticity.

As used herein, "chromaticity" refers to the intensity or vividness of a color or pigment. Chromaticity (C) may further be defined as derived by the parameters L*, a*, and b*, expressed as $[(a^*)^2+(b^*)^2]^{1/2}$. L*, a*, and b* data are described by Richard S. Hunter in *The Measurement of Appearance*, John Wiley & Sons, 1987. These CIELab measurements characterize appearance in terms of lightness-darkness component, represented by L*, red-green component represented by a*, and yellow-blue component represented by b*.

As used herein, the term "optically effective amount" refers to an amount of an effect pigment capable of being detected by the human eye.

As used herein, the term "low refractive index" refers to a material having a refractive index lower than, less than, or equal to about 1.8.

As used herein, the term "high refractive index" refers to a material having a refractive index of greater than or more than about 1.8.

The present methods allow for the production of a semi-transparent effect pigment with improved vibrancy and chromatic colors in a color space not previously accessible. For example, it has been surprisingly found that by modifying the optical thickness of the three inorganic layers a new class of effect pigment material has been obtained. Additionally, the present pigments are entirely inorganic and may be used as replacements for effect pigments containing organic components, such as carmine. Carmine is an organic based pigment, typically available as an extract from beetles.

The pigments of the present application are semitransparent, non-quarter wave, effect pigments that access a new color travel and high chroma color space. The effect pigments demonstrate semitransparent effects in the red, fuchsia, and magenta color space, without utilizing organic pigments. Such effects result from a substrate having multiple inorganic layers as described herein, where the layers have defined refractive indices and optical thickness. In various aspects, effect pigment compositions, methods of making the effect pigment, and product compositions are described herein.

In one aspect, an inorganic, non-quarter wave, heterogeneous multilayer effect pigment is provided that includes a platy substrate, having absorbing optically active metal oxide layer having a thickness of about 20 nm to about 400 nm; a low refractive index material layer on the absorbing optically active metal oxide layer, with the low refractive index material layer having a thickness of about 10 nm to about 500 nm; and an outermost layer of a non-absorbing high refractive index material on the low refractive index material layer, the outermost layer having a thickness of about 50 nm to about 1000 nm. The effect pigment exhibits a blue reflectance ratio ("BRR") of at least 3, as defined by the following equation:

$$BRR = (\text{Blue Max})/(\text{Green Min}).$$

In the equation, Blue Max is the maximum reflectance in the range of about 380 nm to about 450 nm, and the Green Min is the minimum reflectance in the range of about 450 nm to about 600 nm.

Suitable platy substrates, natural or synthetic, may be transparent or semitransparent and sturdy enough to function as a stable support for metal oxide layers. In some embodiments, the platy substrate includes but is not limited to natural mica, synthetic mica, aluminum, glass flakes, $SiO_2$, $Al_2O_3$, talc, bismuth oxychloride, natural pearl, perlite, boron nitride, zinc oxide, a natural silicate, a synthetic silicate, and the like or combinations thereof. In certain embodiments, the platy substrate includes synthetic mica, such as, but not limited to fluorophlogopite.

The effect pigment includes a coating of an absorbing optically active metal oxide layer on the platy substrate. In some embodiments, the absorbing optically active metal oxide layer may have an optical thickness from about 20 nm to about 400 nm. This includes, but is not limited to, an optical thickness from about 25 nm to about 350 nm, from about 30 nm to about 300 nm, from about 35 nm to about 250 nm, or from about 40 nm to about 150 nm. In one embodiment, the absorbing optically active metal oxide layer has an optical thickness from about 40 nm to about 150 nm. In some embodiments, the absorbing optically active metal oxide layer include iron oxides, iron hydroxides, and combinations thereof. In some embodiments, the absorbing optically active metal oxide layer is iron oxide. Suitable iron oxides may include, but are not limited to, hematite, magnetite, or maghemite. In one embodiment, the iron oxide layer includes hematite or maghemite. In another embodiment, the iron oxide layer includes hematite or maghemite and has an optical thickness from about 40 nm to about 150 nm. In yet another embodiment, the iron oxide layer includes hematite or maghemite and has an optical thickness of about 90 nm.

The effect pigment includes a low refractive index material layer coated on the absorbing optically active metal oxide layer. In some embodiments, the low refractive index material layer may have an optical thickness from about 10 nm to about 500 nm. This includes, but is not limited to, an optical thickness from about 20 nm to about 450 nm, from about 20 nm to about 300 nm, from about 20 nm to about 200 nm, from about 100 nm to about 400 nm, or from about 200 nm to about 400 nm. In some embodiments, the low refractive index material layer has an optical thickness from about 20 nm to about 200 nm. In some embodiments, the low refractive index material has a refractive index of less than or equal to 1.8. This includes, but is not limited to, refractive indices from about 1.30 to about 1.80. In one embodiment, the refractive index is from about 1.30 to about 1.50. In another embodiment, the refractive index is from about 1.40 to about 1.50.

In some embodiments, the low refractive index material includes, but is not limited to, silica, magnesium oxide, aluminum oxide, or combinations thereof. In some embodiments, the low refractive index material is silica. This includes amorphous silica. In one embodiment, the low refractive index material includes amorphous silica and has an optical thickness from about 10 nm to about 500 nm.

An outermost layer of the effect pigment includes a non-absorbing high refractive index material layer coated on the low refractive index material layer. In some embodiments, the non-absorbing high refractive index material layer may have an optical thickness from about 50 nm to about 1000 nm. This includes, but is not limited to, an optical thickness from about 50 nm to about 400 nm, about 50 nm to about 200 nm, about 60 nm to about 150 nm, about 200 nm to about 800 nm, or about 500 nm to about 1000 nm. In some embodiments, the non-absorbing high refractive index material layer has an optical thickness from about 60 nm to about 150 nm. In some embodiments, the non-absorbing high refractive index material has a refractive index that is greater than 1.80. This includes, but is not limited to, refractive indices from about 2.00 to about 4.00, about 2.00 to about 3.30, about 2.20 to about 3.00, or about 2.20 to about 2.60. In one embodiment, the refractive index is from about 2.00 to about 3.30. In another embodiment, the refractive index is from about 2.20 to about 2.60.

In some embodiments, the non-absorbing high refractive index material includes but is not limited to titania, zirconium oxide, tin oxide, zinc oxide, or combinations thereof. In some embodiments, the non-absorbing high refractive index material is titania. Suitable types of titania include, but are not limited to, anatase, rutile, or a mixture thereof. In one embodiment, the non-absorbing high refractive index material layer includes rutile and/or anatase titania and has an optical thickness from about 50 nm to about 1000 nm. An advantage of using titania as the non-absorbing high refractive index material includes, but is not limited to, titania having a refractive index of about 2.55.

In order to access the desired color travel and hue color space, the effect pigment of the present technology exhibits a Blue Reflectance Ratio (BRR) of at least 3.00. A BRR of at least 3.00 is illustrative of an effect pigment that exhibits a hue color space that includes red, fuchsia, and/or magenta. The BRR parameters are described in terms Blue Max and Green Min, where the ratio is expressed as:

BRR=(Blue Max)/(Green Min)

The Blue Max represents the maximum reflectance demonstrated by the effect pigment over wavelengths ranging from about 380 nm to about 450 nm. The Green Min represents the minimum reflectance demonstrated wavelengths ranging from about 450 nm to about 600 nm.

In some embodiments, the effect pigment has a BRR of about 3.0 to about 6.0. Suitable BRR values include, but are not limited to, from about 3.0 to about 6.0, about 3.3 to about 6.0, about 3.5 to about 6.0, about 3.8 to about 5.5, or about 4.0 to about 5.5. In one embodiment, the effect pigment has a BRR of about 3.8 to about 5.5. In some embodiments, the Blue Max and Green Min are measured in a lacquer medium. Suitable lacquers include, but are not limited to, nitrocellulose. In one embodiment, the lacquer medium is a nitrocellulose lacquer.

In some embodiments, the Blue Max and Green Min are measured at a 15° observation angle off specular from a 45° illuminant. In one embodiment, the Blue Max and Green Min reflectance spectra are measured using a Byk Mac Spectrophotometer with D65 illuminant at 15° off specular observation angle. It should be noted that for consistency and comparison, the reflectance measurements are as defined as above. Measurements at other angles and with other illuminants illustrate that while the uniqueness of the pigments remain, the specific BRR value will change depending on the illuminant used and the angle measured.

It has been surprisingly found that the effect pigments described herein exhibit the color space described herein in the absence of organic materials. In some embodiments, the effect pigment is free of organic materials. Organic materials may include natural or synthetic materials, such as, but not limited to, carmine.

In one embodiment, the effect pigment includes a platy substrate, having an about 20 nm to about 400 nm thick iron oxide layer; an about 10 nm to about 500 nm thick silica layer on the iron oxide layer; and an about 50 nm to about 1000 nm thick titania layer on the silica layer; where the effect pigment has a BRR of about 3.8 to about 6 measured in a nitrocellulose lacquer medium at a 15° angle off specular from a 45° illuminant.

As described in this application heretofore, the effect pigment of the present technology may be free of organic materials. In some embodiments, the effect material is free of carmine. In some embodiments, the effect pigment may only include an inorganic substrate and inorganic layers.

The effect pigment of the present technology accesses color travel and a hue color space of red, fuchsia, and magenta. In some embodiments, the effect pigment exhibits a chromaticity (15° C.*) of greater than about 50. In some embodiments, the effect pigment exhibits a chromaticity of about 50 to about 80. Suitable chromaticity includes, but is not limited to, about 50 to about 80, about 60 to about 80, about 65 to about 80, about 70 to about 80, and ranges between any two of these values or less than one of these values. In one embodiment, the effect pigment exhibits a chromaticity of about 70. In some embodiments, the effect pigment exhibits a hue of about 20 to about 320. Suitable hues include, but are not limited to, about 20 to about 320, about 15 to about 330, about 5 to about 330, about 360 to about 340, and ranges between any two of these values or less than any one of these values. In one embodiment, the effect pigment exhibits a hue of about 20 to about 330. In another embodiment, the effect pigment exhibits a hue of about 345.

In one embodiment, the effect pigment includes a platy substrate having an iron oxide layer on the platy substrate; a silica layer on the iron oxide layer; and a titania layer on the silica layer; where the iron oxide layer has an optical thickness from about 20 nm to about 400 nm, the silica layer has an optical thickness from about 10 nm to about 500 nm, and the titania layer has an optical thickness from about 50 nm to about 1000 nm; and where the effect pigment is free of organic materials and exhibits an absorption in the region of 580 nm to 750 nm, chromaticity from about 50 to about 80, and a hue from about 20 to about 320.

In another aspect, methods are provided for producing an effect pigment as described above. The method may include coating a platy substrate with an optical coating, the coating includes depositing an absorbing optically active metal oxide layer on the platy substrate, the absorbing optically active metal oxide layer having an optical thickness of about 20 nm to about 400 nm; depositing a low refractive index material layer on the absorbing optically active metal oxide layer, the low refractive index material layer having an optical thickness of about 10 nm to about 500 nm; and depositing a non-absorbing high refractive index material layer on the low refractive index material layer, the non-absorbing high refractive index material layer having a thickness from about 50 nm to 1000 nm; and where the effect pigment exhibits a BRR of at least 3.

As noted above, the methods include coating the platy substrate with an optical coating, the optical coating includes depositing an absorbing optically active metal oxide layer on the platy substrate. This includes, but is not limited to, the absorbing optically active metal oxides as described above in any embodiment. In some embodiments, the method includes depositing the absorbing optically active metal oxide layer to an optical thickness from about 20 nm to about 400 nm. In one embodiment, the depositing includes reaching an optical thickness of 25 nm to about 350 nm, from about 30 nm to about 300 nm, from about 35 nm to about 250 nm, or from about 40 nm to about 150 nm. In some embodiments, the depositing includes reaching an optical thickness from about 40 nm to about 150 nm.

The coating further includes depositing a low refractive index material layer on the absorbing optically active metal oxide layer. The low refractive index material layer includes those described above in any embodiment, including but not limited to silica. The method includes depositing the low refractive index material layer to an optical thickness from about 10 nm to about 500 nm. Suitable optical thicknesses may include, but are not limited to, from about 20 nm to about 450 nm, from about 20 nm to about 300 nm, from about 20 nm to about 200 nm, from about 100 nm to about 400 nm, or from about 200 nm to about 400 nm. In some embodiments, the depositing includes reaching a low refractive index material layer optical thickness from about 20 nm to about 200 nm.

In the methods, the coating further includes depositing a non-absorbing high refractive index material layer on the low refractive index material layer. The non-absorbing high refractive index material layer includes those described above in any embodiment. In some embodiments, the non-absorbing high refractive index material includes titania as described above in any embodiment. The method further includes depositing the non-absorbing high refractive index material layer to an optical thickness from about 50 nm to about 1000 nm. Suitable non-absorbing high refractive index optical thicknesses include, but are not limited to, from about 50 nm to about 400 nm, about 50 nm to about 200 nm, about 60 nm to about 150 nm, about 200 nm to about 800 nm, or about 500 nm to about 1000 nm. In some embodiments, the depositing includes reaching an optical thickness from about 60 nm to about 150 nm.

The depositing may include, but is not limited to, chemical vapor deposition (CVD), physical vapor deposition (PVD), and wet-chemical methods. In some embodiments, the depositing includes a wet-chemical method.

In the method, where the non-absorbing high refractive index material is titania, prior to depositing the titania layer, the method may further include pre-treating the low refractive index material layer with a rutile directing agent. This includes treating the low refractive index material layer with $SnCl_4$ before depositing titania. An advantage of treating the low refractive index material layer with $SnCl_4$ includes, but is not limited to, formation of rutile titania which has a higher refractive index than anatase titania.

As described above in any embodiment, the method includes producing an effect pigment that exhibits a chromaticity of greater than about 50. In some embodiments, the method further includes producing an effect pigment that exhibits a hue of about 20 to about 320. In some embodiments, the method includes producing an effect pigment having a BRR from about 3.0 to about 6.0. In some embodiments, the method includes producing an effect pigment that is free of organic material, as described above in any embodiment.

In one embodiment, the method includes producing an effect pigment, as described above in any embodiment, that includes coating a platy substrate with an optical coating having the steps of depositing an iron oxide layer to an optical thickness from about 20 nm to about 400 nm; depositing a silica layer to an optical thickness of about 10 nm to about 500 nm; and depositing a titania layer to an optical thickness from about 500 nm to about 1000 nm; where the effect pigment is free of organic material and exhibits a hue of about 350 to about 330, a chromaticity of about 50 to about 80, a BRR of greater than 3, and absorption in the region of 580 nm to 750 nm.

In yet another aspect, products are provided that include the effect pigment as described herein. Such products may include, but are not limited to, cosmetics, automotive coatings, industrial coatings, inks, plastics, and the like.

In some embodiments, the product includes cosmetic products that include the effect pigments. In some embodiments, the cosmetic product further includes a suitable carrier. Suitable carriers include, but are not limited to, gels, emulsions, creams, waxes, compacts, and the like or combinations thereof.

The cosmetic product may be in the form of a cream, emulsion, milk, foam, gel, lotion, mousse, ointment, past, powder, spray, suspension, and the like or combinations thereof. In some embodiments, the cosmetic product of the present technology, while not limited to a particular type, may include a concealing stick, foundation, stage make-up, mascara, eye shadow, hair color, lipstick, lip gloss, kohl pencil, eye liner, blusher, eyebrow pencil, cream powder, nail enamel, skin glosser stick, hair spray, face powder, leg-makeup, insect repellent lotion, nail enamel remover, perfume lotion, or shampoo.

In another aspect of the present technology, a method of changing the appearance of the skin is provided herein, the method includes applying an optically effective amount of the effect pigment or a composition or product containing the effect pigment to the skin of an individual.

The present technology, thus generally described, will be understood more readily by reference to the following examples, which are provided by way of illustration and are not intended to be limiting of the present technology.

EXAMPLES

Example 1

A 6.5% aqueous slurry containing 130 g synthetic mica flakes (d50 approximately 20 μm) was heated to 82° C. and stirred. The pH of the slurry was adjusted to 3.0 with HCl. Then, 620 grams of 39% $FeCl_3.5H_2O$ were added at 2 g/min while the pH was maintained with a NaOH solution. Calcination of a pigment sample resulted in a hue of 20°. At the desired shade, the pH of the slurry was raised to 7.8 with NaOH and 700 g of 20% $Na_2SiO_3.5H_2O$ were added at 2 g/min while the pH was maintained at 7.80 by the addition of an HCl solution. After the addition of the 20% $Na_2SiO_3.5H_2O$ was complete, the pH of the slurry was adjusted to 1.5 with HCl. Then, 20 g of 20% $SnCl_4.5H_2O$ were added at 1.5 g/min while the pH was maintained with the addition of NaOH solution. The slurry was stirred, followed by the addition of 700 g 40% $TiCl_4$ at 2 g/min while the pH was maintained at 1.50 by the addition of NaOH solution. Next, 50 mL of the slurry was filtered, and the presscake was washed with water and calcined at 850° C. for 20 minutes. The sample was drawn down for color measurement. The resulting hue was 4°, the chroma was 67, and the BRR was 5.24.

Example 2

Example 2 was run on the same procedure set forth in Example 1 except 40 g of 20% $SnCl_4.5H_2O$ and 750 g 40% $TiCl_4$ were deposited on the final layer. 50 mL of the slurry was filtered, and the presscake was washed with water and calcined at 850° C. for 20 minutes. The sample was drawn down for color measurement. The resulting hue was 346°, the chroma was 70, and the BRR was 4.99.

Example 3

Example 3 was run on the same procedure set forth in Example 1 except 400 g of 20% $Na_2SiO_3.5H_2O$, 10 g of 20% $SnCl_4.5H_2O$, and 800 g 40% $TiCl_4$ were deposited on the final layer. 50 mL of the slurry was filtered, and the presscake was washed with water and calcined at 850° C. for 20 minutes. The sample was drawn down for color measurement. The resulting hue was 331°, the chroma was 68, and the BRR was 4.41.

Example 4

Example 4 was run with a similar procedure set forth in Example 1 except the mica flakes had a d50 of 12 μm, 100 g of substrate were used, and the amounts of iron, silica, tin and titania were varied. 600 g of $FeCl_3.5H_2O$ were added resulting in a hue of 25. 800 g of $Na_2SiO_3.5H_2O$, 60 g of 20% $SnCl_4.5H_2O$, and 800 g 40% $TiCl_4$ were deposited on the final layer. The resulting sample had a hue of 346, a chroma of 62, and a BRR of 3.99.

Example 5

Example 5 was run with a similar procedure set forth in Example 1 except the natural mica flakes had a d50 of 70 μm and 320 g of substrate was used. 800 g of $FeCl_3.5H_2O$ were added resulting in a hue of 15. 625 g of $Na_2SiO_3.5H_2O$, 30 g of 20% $SnCl_4.5H_2O$, and 700 g 40% $TiCl_4$ were deposited on the final layer. The resulting sample had a hue of 332, a chroma of 59, and a BRR of 3.67.

Example 6

Example 6 was run with a similar procedure set forth in Example 1 except the substrate was glass flakes with a d50 of 80 μm, 215 g of substrate was used. 500 g of $FeCl_3.5H_2O$ were added resulting in a hue of 17. 400 g of $Na_2SiO_3.5H_2O$, 15 g of 20% $SnCl_4.5H_2O$, and 400 g 40% $TiCl_4$ were deposited on the final layer. The resulting sample had a hue of 334, a chroma of 56, and a BRR of 4.13.

Example 7

Example 7 was run with a similar procedure set forth in Example 1 except the substrate was natural mica flakes with a d50 of 20 μm. 550 g of $FeCl_3.5H2O$ were added resulting in a hue of 17. 500 g of $Na_2SiO_3.5H_2O$, 55 g of 20% $SnCl_4.5H2O$, and 800 g 40% $TiCl_4$ were deposited on the final layer. The resulting sample had a hue of 332, a chroma of 70, and a BRR of 4.63.

Example 8

Example 8 was run with a similar procedure set forth in Example 1. 600 g of $FeCl_3.5H_2O$ were added resulting in a hue of 355. 600 g of $Na_2SiO_3.5H_2O$, 20 g of 20% $SnCl_4.5H_2O$, and 800 g 40% $TiCl_4$ were deposited on the final layer. The resulting sample had a hue of 332, a chroma of 80, and a BRR of 5.63.

Example 9

Example 9 was run with a similar procedure set forth in Example 1. 500 g of $FeCl_3.5H_2O$ were added resulting in a hue of 25. 625 g of $Na_2SiO_3.5H_2O$, 35 g of 20% $SnCl_4.5H_2O$, and 650 g 40% $TiCl_4$ were deposited on the final layer. The resulting sample had a hue of 21, a chroma of 67, and a BRR of 4.76.

Example 10

BRR values were evaluated for comparative commercial pigments that access a similar color space as the present technology. Table 1 provides BRR, hue, and chroma values for Examples 1-9 and commercial pigments. Commercial pigments exhibiting BRR values above about 3 do not have a first layer of iron oxide and also use an organic dye, such as carmine. Commercial pigments that have a first layer of iron oxide failed to exhibit BRR values above about 3. In contrast, Examples 1-9 prepared according to the present technology exhibited BRR values of greater than about 3.

TABLE 1

Example Effect Pigments vs. Commercial Samples

| Effect Pigment | Hue | Chroma | BRR | First Layer Fe |
| --- | --- | --- | --- | --- |
| Example 1 | 4 | 67 | 5.24 | Yes |
| Example 2 | 346 | 70 | 4.99 | Yes |
| Example 3 | 331 | 68 | 4.41 | Yes |
| Example 4 | 346 | 62 | 3.99 | Yes |
| Example 5 | 332 | 59 | 3.67 | Yes |
| Example 6 | 334 | 56 | 4.13 | Yes |
| Example 7 | 332 | 70 | 4.63 | Yes |
| Example 8 | 332 | 80 | 5.63 | Yes |
| Example 9 | 21 | 67 | 4.76 | Yes |
| Cloisonne Super Rouge 450Z | 20 | 60 | 1.63 | Yes |
| Cloisonne Cerise Flambe 550Z | 11 | 56 | 1.80 | Yes |
| Cloisonne Blue Flambe 650Z | 357 | 42 | 1.92 | Yes |
| Cloisonne Super Red 434Z | 352 | 51 | 5.28 | No |
| Cloisonne Vivid Red 450 DHCB | 351 | 58 | 3.59 | No |
| Gemtone Amethyst | 340 | 42 | 4.44 | No |
| Cloisonne Violet 525C | 306 | 67 | 5.50 | No |
| SynMira ROG25 | 31 | 59 | 2.49 | Yes |
| SunPearl Maroon | 27 | 56 | 1.39 | Yes |
| Xirona le Rouge | 27 | 85 | 2.48 | Yes |
| MIRAGE Sparkling Fire Red | 21 | 43 | 1.43 | Yes |
| Colorona Sienna | 18 | 59 | 1.61 | Yes |
| Colorona SynCranberry | 16 | 60 | 1.75 | Yes |
| Colorona Glitter Bordeaux | 2 | 34 | 1.52 | Yes |
| Colorona SynBerry Pink | 349 | 53 | 6.69 | No |
| Colorona Patagonian Purple | 304 | 39 | 3.23 | No |
| Colorona Magenta | 277 | 61 | 5.41 | No |
| MIRAGE Glamour Sapphire | 262 | 41 | 3.93 | No |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An inorganic, non-quarter wave, heterogeneous multilayer effect pigment comprising:
    a platy substrate comprising an absorbing optically active metal oxide layer thereon, having an optical thickness from about 20 nm to about 400 nm;
    a layer of low refractive index material on the absorbing optically active metal oxide layer and having an optical thickness from about 10 nm to about 500 nm; and
    an outermost optically active layer of a non-absorbing high refractive index material on the low refractive index material and having an optical thickness from about 50 nm to about 1000 nm;
    wherein:
    the multilayer effect pigment has a hue color space of red, fuchsia, and/or magenta color; and the multilayer effect pigment has a chromaticity (15° C.*) of greater than 50 to about 80; the multilayer effect pigment exhibits a blue reflectance ratio (BRR) of at least 3, according to the equation:

BRR=(Blue Max)/(Green Min)

Blue Max is the maximum reflectance exhibited over wavelengths 380 nm to 450 nm; and Green Min is the minimum reflectance exhibited over wavelengths 450 nm to 600 nm,
    wherein the Blue Max and Green Min are measured using a Byk Mac Spectrophotometer with D65 illuminant at 15° off specular observation angle.

2. The effect pigment of claim 1, wherein the platy substrate comprises a synthetic mica, wherein the absorbing optically active metal oxide layer has an optical thickness of from 40 nm to 150 nm, wherein the low refractive index material layer has an optical thickness of from 20 nm to 200 nm, and wherein the non-absorbing high refractive index material layer has an optical thickness of from 60 nm to 150 nm; and
    wherein the platy substrate comprises natural mica and/or synthetic mica,
    wherein the absorbing optically active metal oxide layer comprises iron oxide,
    wherein the low refractive index layer comprises silica; and
    wherein the high refractive index layer comprises titania.

3. The effect pigment of claim 2, wherein the iron oxide layer comprises hematite, magnetite, or maghemite, wherein the silica comprises amorphous silica, wherein the titania comprises anatase, rutile, or a mixture thereof.

4. The effect pigment, of claim 3, wherein the non-absorbing high refractive index material has a refractive index of n>1.8 and wherein the low refractive index material has a refractive index of n<1.8.

5. The effect pigment of claim 4, wherein the non-absorbing high refractive index material layer has a refractive index of about 2.00 to about 3.30.

6. The effect pigment of claim 4, wherein the BRR is from about 3.5 to about 6.

7. The effect pigment of claim 6, wherein the BRR is about 3.8 to about 5.5.

8. The effect pigment of claim 4, wherein the effect pigment is free of organic material.

9. The effect pigment of claim 4, wherein the effect pigment consists of an inorganic substrate and inorganic layers.

10. A product comprising the effect pigment of claim 1.

11. The product of claim 10, wherein the product comprises cosmetics, automotive coatings, industrial coatings, inks, and plastics.

\* \* \* \* \*